(12) United States Patent
France

(10) Patent No.: US 6,843,105 B1
(45) Date of Patent: Jan. 18, 2005

(54) CONTACT PIN FOR EXHAUST GAS SENSOR

(75) Inventor: Ken France, Clemson, SC (US)

(73) Assignee: Robert Bosch Corporation, Broadview, IL (US)

( * ) Notice: Subject to any disclaimer, the term of this patent is extended or adjusted under 35 U.S.C. 154(b) by 0 days.

(21) Appl. No.: 10/610,479

(22) Filed: Jun. 30, 2003

(51) Int. Cl.[7] .................................................. G01N 27/00
(52) U.S. Cl. ..................... 73/31.05; 73/23.31; 204/424
(58) Field of Search ........................... 73/23.31, 23.32, 73/31.05; 204/424–429

(56) References Cited

U.S. PATENT DOCUMENTS

| | | |
|---|---|---|
| 2,879,583 A | 3/1959 | Booth et al. |
| 3,007,810 A | 11/1961 | Hobrock |
| 3,574,033 A | 4/1971 | Kolkman et al. |
| 3,916,071 A | 10/1975 | Kinnebrew et al. |
| 4,001,758 A | 1/1977 | Esper et al. |
| 4,107,018 A | 8/1978 | Bode et al. |
| 4,127,424 A | 11/1978 | Ullery, Jr. |
| 4,130,797 A | 12/1978 | Hattori et al. |
| 4,133,910 A | 1/1979 | Ruwe et al. |
| 4,155,827 A | 5/1979 | Maurer et al. |
| 4,212,720 A | 7/1980 | Maurer et al. |
| 4,264,647 A | 4/1981 | Trevorrow |
| 4,296,148 A | 10/1981 | Friese |
| 4,305,803 A | 12/1981 | Beyer et al. |
| 4,310,401 A | 1/1982 | Stahl |
| 4,338,362 A | 7/1982 | Turcotte |
| 4,339,320 A | 7/1982 | Friese et al. |
| 4,413,502 A | 11/1983 | Ohta et al. |
| 4,419,212 A | 12/1983 | Dietz et al. |
| 4,490,411 A | 12/1984 | Feder |
| 4,504,522 A | 3/1985 | Kaiser et al. |
| 4,540,479 A | 9/1985 | Sakurai et al. |
| 4,595,614 A | 6/1986 | Nunlist |
| 4,597,850 A | 7/1986 | Takahasi et al. |
| 4,773,376 A | 9/1988 | Uchikawa et al. |

(List continued on next page.)

FOREIGN PATENT DOCUMENTS

| | | |
|---|---|---|
| DE | 19614147 A | 6/2000 |
| JP | 52-94195 A | 8/1977 |
| JP | 57-182158 A | 11/1982 |
| JP | 61-79677 A | 4/1986 |
| JP | 62-53765 A | 3/1987 |
| JP | 5-64762 A | 3/1993 |
| JP | 9-26034 A | 1/1997 |
| JP | 9-75810 A | 3/1997 |
| JP | 9-72876 A | 6/1998 |
| WO | WO 62644 A | 9/1999 |

OTHER PUBLICATIONS

Description of Prior Art Sensors Shown in Photos; 4 pages.
SAE International; Surface Vehicle Standard; SAE J548–1 for spark plugs; Jul., 1996; pp. 1–18; Warrendale, PA.
Unpublished, pending U.S. patent application No. 10/274,305 filed Oct. 18, 2002.

*Primary Examiner*—Daniel S. Larkin
(74) *Attorney, Agent, or Firm*—Michael Best & Friedrich LLP

(57) ABSTRACT

An exhaust gas sensor includes a sensor element configured to communicate with an exhaust gas of an internal combustion engine, and a contact pin assembly including a first portion configured to be electrically connected to the sensor element when the contact pin assembly is installed in the exhaust gas sensor. The contact pin assembly also includes a second portion configured to be connected to the first portion in either of a first configuration, in which the contact pin assembly has a first overall length, and a second configuration, in which the contact pin assembly has a second overall length less than the first overall length. The second portion is selectively connected to the first portion in the first configuration or the second configuration depending on a length of the exhaust gas sensor.

22 Claims, 11 Drawing Sheets

U.S. PATENT DOCUMENTS

| | | |
|---|---|---|
| 4,943,330 A | 7/1990 | Iino et al. |
| 5,017,340 A | 5/1991 | Pribat et al. |
| 5,032,568 A | 7/1991 | Lau et al. |
| 5,096,734 A | 3/1992 | Nikulainen et al. |
| 5,139,639 A | 8/1992 | Holleboom |
| 5,169,513 A | 12/1992 | Mase et al. |
| 5,329,806 A | 7/1994 | McClanahan et al. |
| 5,346,605 A | 9/1994 | Wolcott et al. |
| 5,372,775 A | 12/1994 | Hayashi et al. |
| 5,423,972 A | 6/1995 | Mann et al. |
| 5,522,979 A | 6/1996 | Tatumoto et al. |
| 5,546,787 A | 8/1996 | Hafele et al. |
| 5,573,650 A | 11/1996 | Fukaya et al. |
| 5,670,032 A | 9/1997 | Friese et al. |
| 5,711,863 A | 1/1998 | Henkelmann et al. |
| 5,736,095 A | 4/1998 | Shimada et al. |
| 5,739,414 A | 4/1998 | Paulus et al. |
| 5,780,100 A | 7/1998 | McCabe et al. |
| 5,817,920 A | 10/1998 | Kuisell et al. |
| 5,846,391 A | 12/1998 | Friese et al. |
| 5,886,248 A | 3/1999 | Paulus et al. |
| 5,900,129 A | 5/1999 | Tsuji et al. |
| 5,922,938 A | 7/1999 | Hafele |
| 5,935,399 A | 8/1999 | Tanaka et al. |
| 5,942,092 A | 8/1999 | Weyl et al. |
| 5,948,225 A | 9/1999 | Katafuchi et al. |
| 5,955,656 A | 9/1999 | Graser et al. |
| 6,063,249 A | 5/2000 | Duce et al. |
| 6,068,746 A | 5/2000 | Kojima et al. |
| 6,074,694 A | 6/2000 | Friese et al. |
| 6,082,175 A | 7/2000 | Yoshikawa et al. |
| 6,096,372 A | 8/2000 | Nomura et al. |
| 6,164,120 A | 12/2000 | Friese et al. |
| 6,206,377 B1 | 3/2001 | Weyl |
| 6,266,997 B1 | 7/2001 | Nelson |
| 6,273,432 B1 | 8/2001 | Weyl et al. |
| 6,319,376 B1 | 11/2001 | Graser et al. |
| 6,342,141 B1 | 1/2002 | Nelson |
| 6,408,680 B2 | 6/2002 | Friese et al. |
| 2004/0074284 A1 * | 4/2004 | Day et al. .................. 73/23.31 |

* cited by examiner

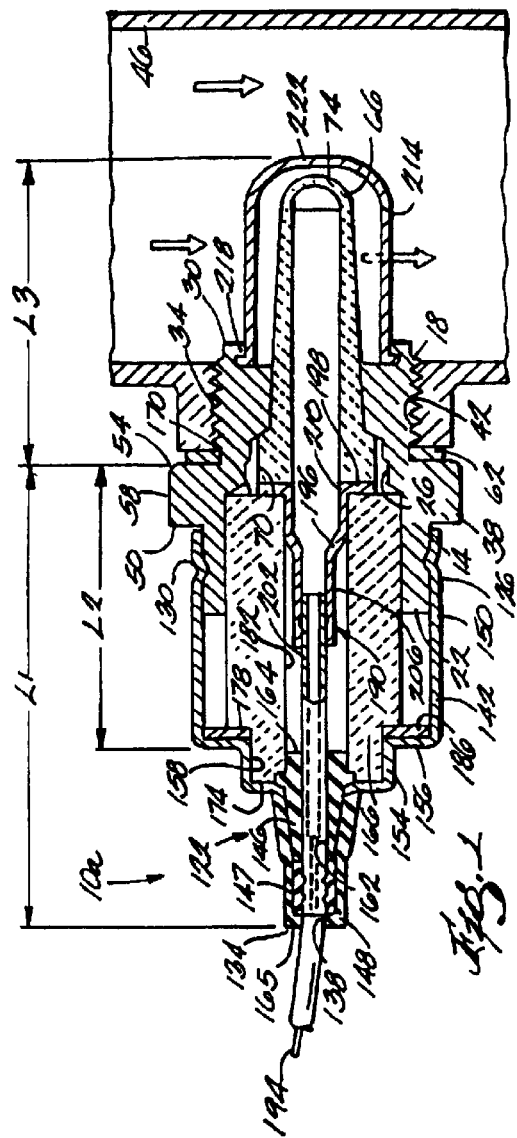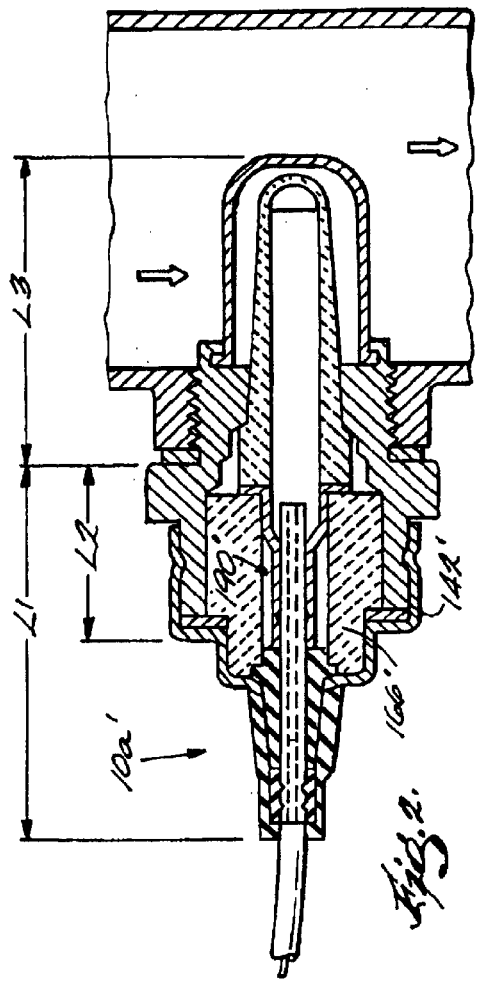

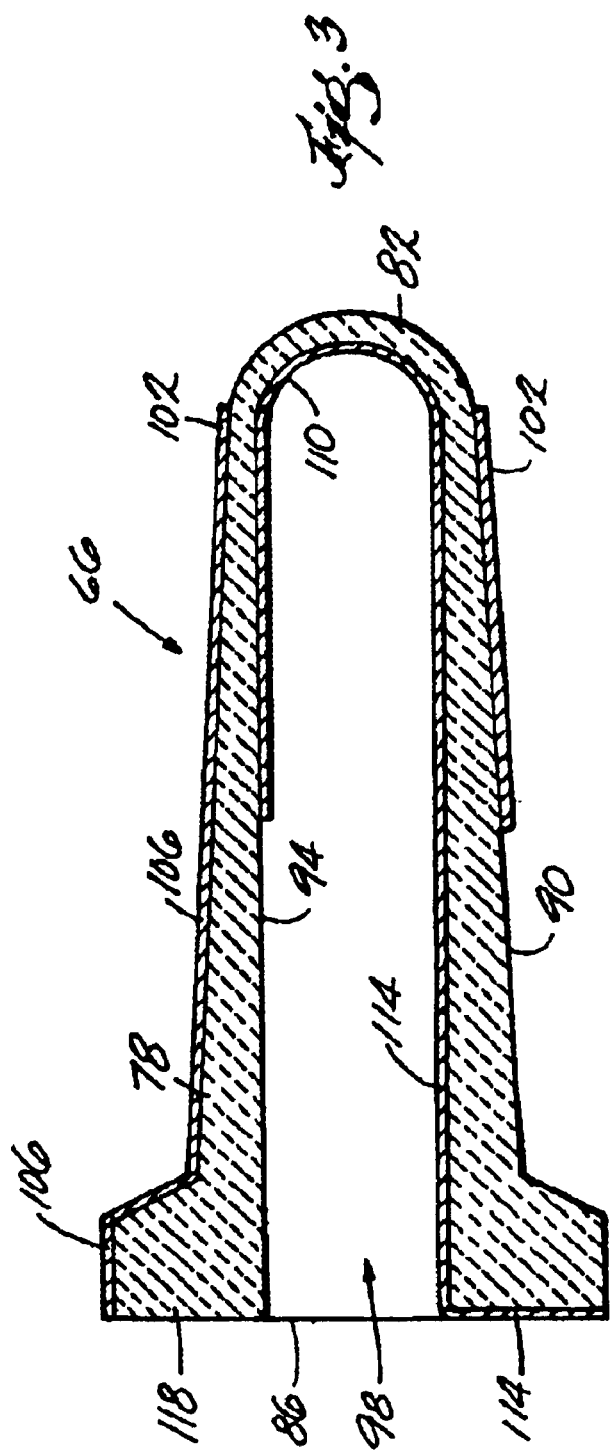

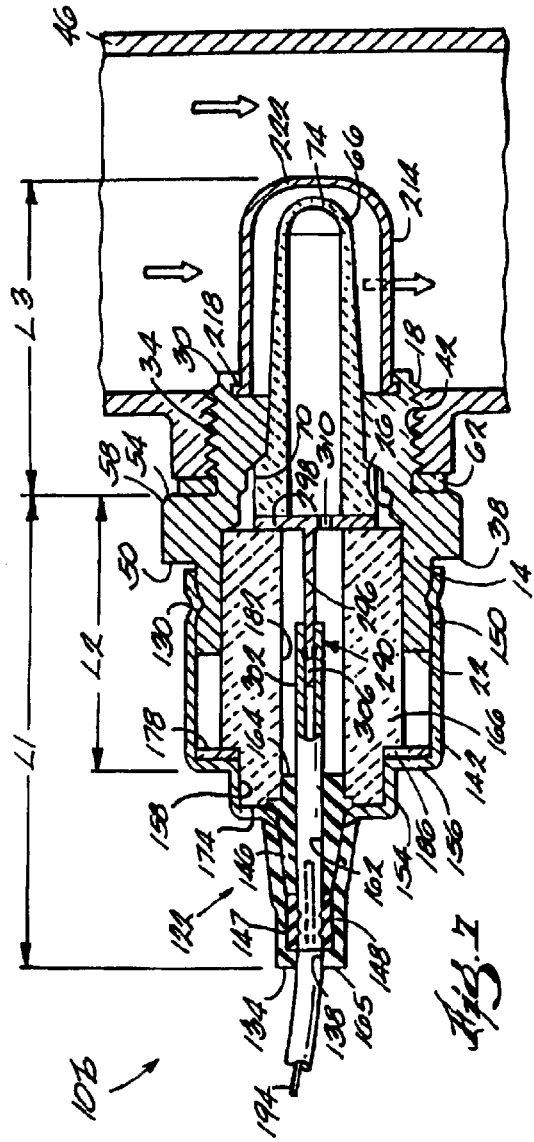
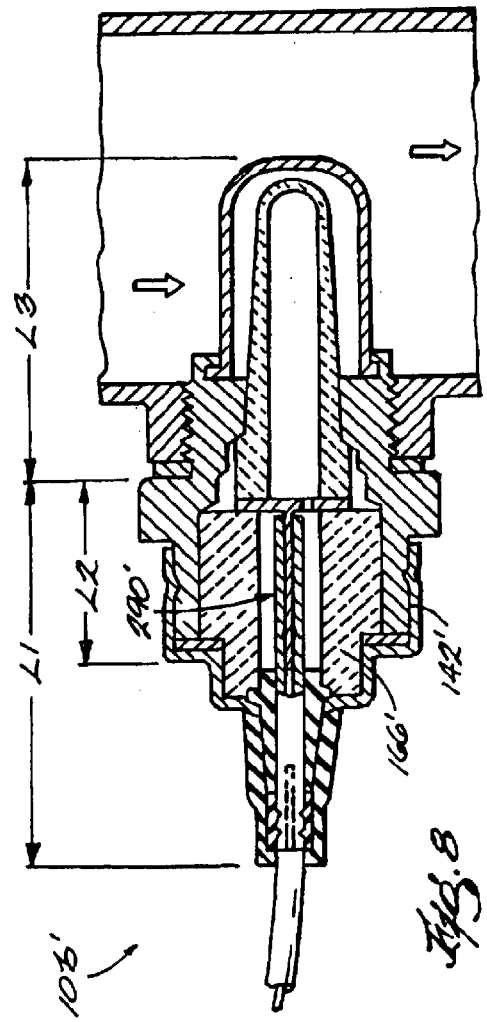

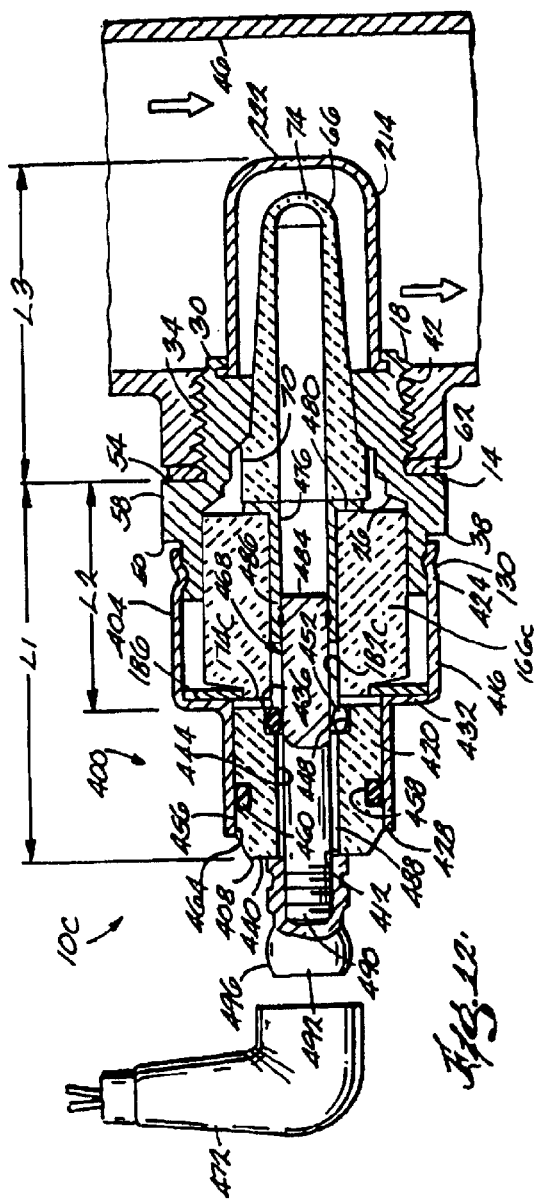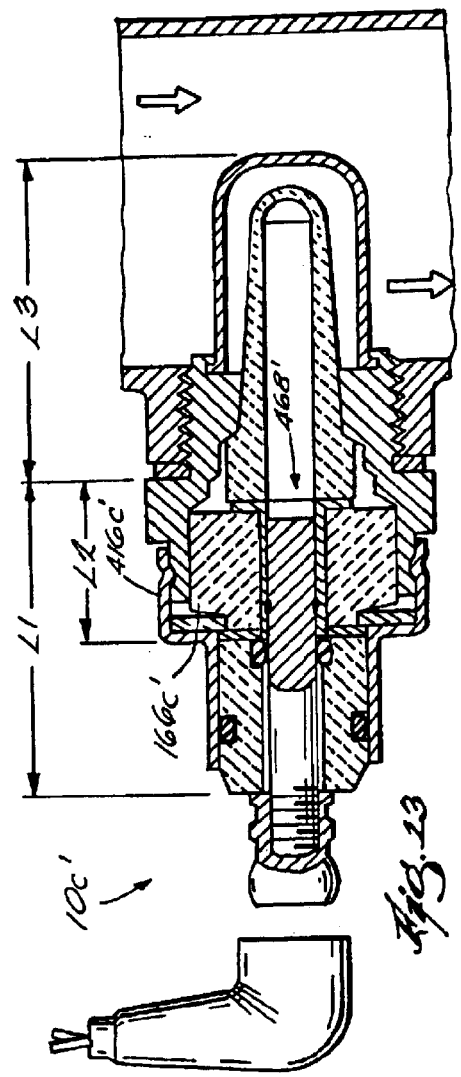

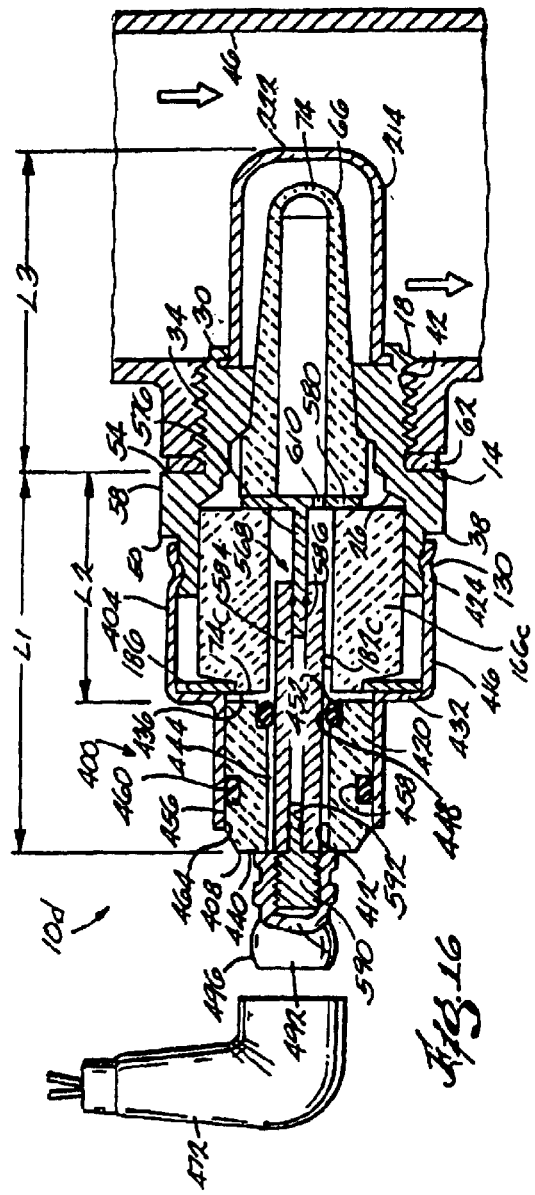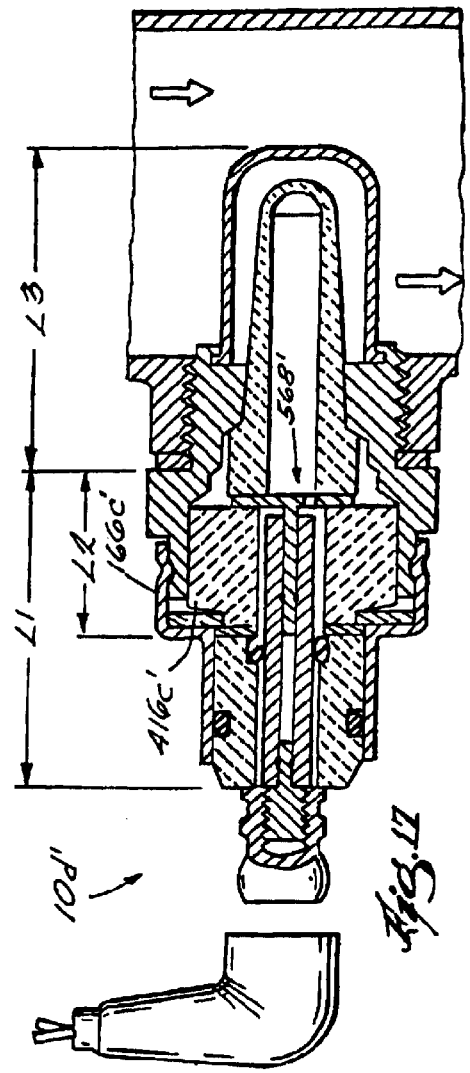

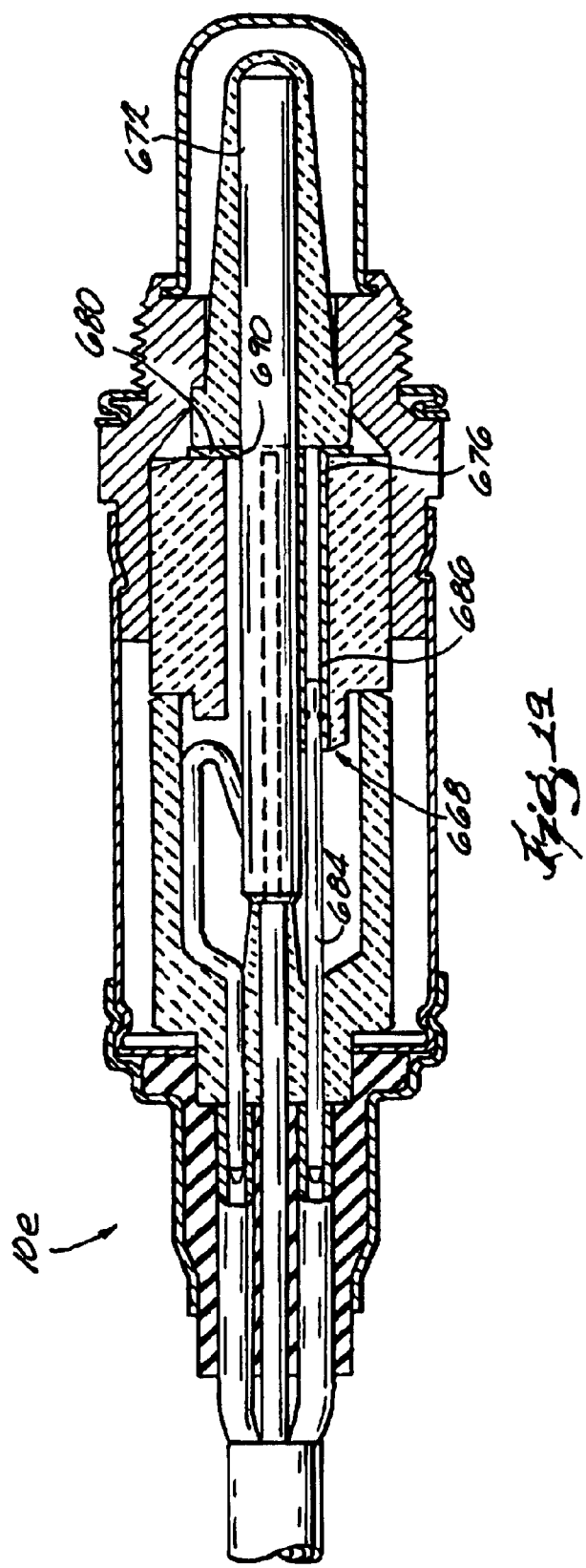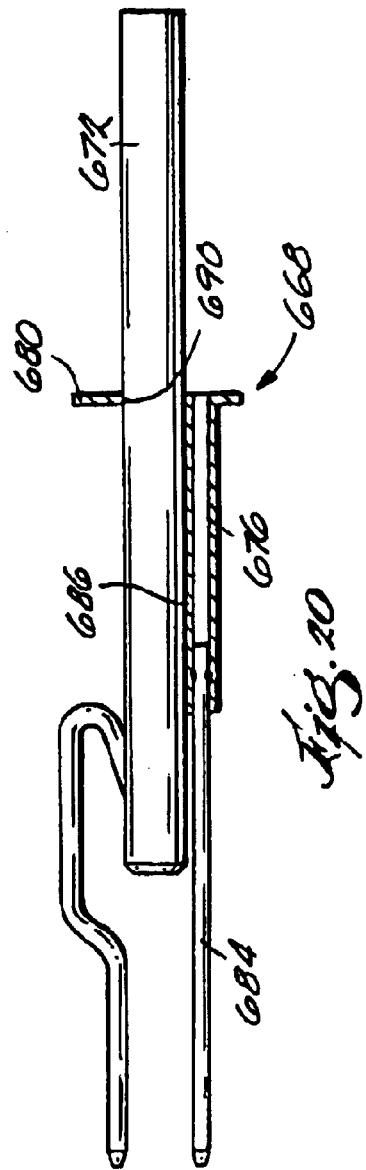

US 6,843,105 B1

CONTACT PIN FOR EXHAUST GAS SENSOR

FIELD OF THE INVENTION

The invention relates to exhaust gas sensors.

BACKGROUND OF THE INVENTION

Exhaust gas sensors are well known in the automotive industry for sensing the oxygen, carbon monoxide, or hydrocarbon content of the exhaust stream generated by internal combustion engines. Stoichiometric or "Nernst"-type oxygen sensors (a widely used type of exhaust gas sensor) measure the difference between the partial pressure of oxygen found in the exhaust gas and oxygen found in the atmosphere. By determining the amount of oxygen in the exhaust gas, the oxygen sensor enables the engine control unit to adjust the air/fuel mixture and achieve optimal engine performance. Other types of exhaust gas sensors that operate based on different principles are also known and widely used in the automotive industry.

SUMMARY OF THE INVENTION

The invention provides an improved contact pin assembly, the length of which can be adjusted for use with exhaust gas sensors of varying length. The adjustable length contact pin assembly of the invention reduces or eliminates the need for manufacturing multiple contact pins of different lengths. The invention is particularly useful for sensors like those disclosed in pending U.S. application Ser. No. 10/274,305, filed Oct. 18, 2002, assigned to Robert Bosch Corporation, and hereby incorporated by reference. The sensors disclosed in pending U.S. application Ser. No. 10/274,305 and the present application can be manufactured in different lengths to suit the specific application in which they will be used, based largely on the operating temperatures of the specific internal combustion engine. The single contact pin assembly of the invention can be used to accommodate the available range of sensor lengths.

More specifically, the invention provides a contact pin assembly for an exhaust gas sensor having a sensor element. The contact pin assembly includes a first portion configured to be electrically connected to the sensor element when the contact pin assembly is installed in the exhaust gas sensor, and a second portion configured to be connected to the first portion in either of a first configuration, whereby the contact pin assembly has a first overall length, and a second configuration, whereby the contact pin assembly has a second overall length less than the first overall length.

The invention also provides an exhaust gas sensor including a sensor element configured to communicate with an exhaust gas of an internal combustion engine, and a contact pin assembly electrically connected to the sensor element. The contact pin assembly includes a first portion configured to engage the sensor element, and a second portion configured to be connected to the first portion in either of a first configuration, whereby the contact pin assembly has a first overall length, and a second configuration, whereby the contact pin assembly has a second overall length less than the first overall length. The second portion is selectively connected to the first portion in the first configuration or the second configuration depending on the length of the exhaust gas sensor.

Further, the invention provides a method of assembling an exhaust gas sensor having a sensor element and a contact pin assembly electrically connected to the sensor element. The contact pin assembly has a first portion configured to engage the sensor element and a second portion configured to be connected to the first portion in either of a first configuration, where the contact pin assembly has a first overall length, and a second configuration, where the contact pin assembly has a second overall length. The method includes determining a length of the exhaust gas sensor. The method also includes connecting the second portion to the first portion in one of the first and second configurations depending on the length of the exhaust gas sensor. Further, the method includes installing the contact pin assembly in the exhaust gas sensor after connecting the second portion to the first portion.

Other features and advantages of the invention will become apparent to those skilled in the art upon review of the following detailed description, claims, and drawings.

BRIEF DESCRIPTION OF THE DRAWINGS

FIG. 1 is a cross-sectional view of an exhaust gas sensor including a contact pin assembly of the invention shown in a first configuration.

FIG. 2 is a cross-sectional view of an exhaust gas sensor similar to the sensor of FIG. 1, but with a shorter body length and showing the contact pin assembly in a second configuration.

FIG. 3 is an enlarged cross-sectional view of the cup-shaped ceramic member shown in FIGS. 1 and 2.

FIG. 7 is a cross-sectional view of an exhaust gas sensor including a second contact pin assembly of the invention shown in a first configuration.

FIG. 8 is a cross-sectional view of an exhaust gas sensor similar to the sensor of FIG. 7, but with a shorter body length and showing the second contact pin assembly in a second configuration.

FIG. 12 is a cross-sectional view of an exhaust gas sensor including a third contact pin assembly of the invention shown in a first configuration.

FIG. 13 is a cross-sectional view of an exhaust gas sensor similar to the sensor of FIG. 12, but with a shorter body length and showing the third contact pin assembly in a second configuration.

FIG. 16 is a cross-sectional view of an exhaust gas sensor including a fourth contact pin assembly of the invention shown in a first configuration.

FIG. 17 is a cross-sectional view of an exhaust gas sensor similar to the sensor of FIG. 16, but with a shorter body length and showing the fourth contact pin assembly in a second configuration.

FIG. 19 is a cross-sectional view of a heated exhaust gas sensor including a fifth contact pin assembly of the invention shown in a first configuration.

FIG. 20 is a cross-sectional view of the fifth contact pin assembly of FIG. 19 shown with a heating element.

FIG. 21 is a graph illustrating the relationship between the temperature of the hex portion of an exhaust gas sensor and the minimum body length for the sensor, where two different grommets are used.

Figure 4:
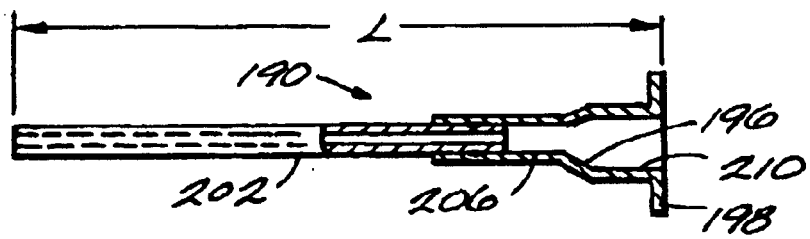
FIG. 4 is a cross-sectional view of the contact pin assembly of FIGS. 1 and 2 shown in the first configuration.

Before one construction of the invention is explained in detail, it is to be understood that the invention is not limited in its application to the details of construction and the arrangements of the components set forth in the following description or illustrated in the drawings. The invention is capable of other constructions and of being practiced or being carried out in various ways. Also, it is understood that the phraseology and terminology used herein is for the purpose of description and should not be regarded as limiting. The use of "including" and "comprising" and variations thereof herein is meant to encompass the items listed thereafter and equivalents thereof as well as additional items.

DETAILED DESCRIPTION

FIG. 1 illustrates a first miniaturized exhaust gas sensor 10a according to the invention. The illustrated sensor 10a is a case-grounded, unheated, single wire sensor, however, those skilled in the art will understand that the sensor 10a could be modified to be a heated, multiple-wire sensor.

The sensor 10a includes a generally cylindrical metallic housing 14 having a first end 18 and a second end 22. A bore 26 extends through the housing 14 from the end 18 to the end 22. The purpose of the bore will be explained in greater detail below. In the illustrated construction, the housing 14 includes a crimp shoulder 30 adjacent the end 18, a threaded portion 34 extending from near the crimp shoulder 30 toward the end 22, and a nut or hex portion 38 between the threaded portion 34 and the end 22. The threaded portion 34 is configured to be received in a threaded aperture 42 of an exhaust pipe 46 or other component (not shown) of an internal combustion engine (not shown) used for non-automotive applications, such as motorcycles, snowmobiles, ATV's, lawnmowers, and the like.

The nut portion 38 includes a first end surface 50, a second end surface 54 and a hexagonal outer surface 58 extending between the surfaces 50 and 54. The hexagonal outer surface 58 is configured to receive a tool, such as a crescent wrench or a socket wrench (not shown), that can be used to tighten the housing 14 in the threaded aperture 42. A washer 62 is preferably mounted on the housing 14 between the threaded portion 34 and the end surface 54 of the nut portion 38 so that the end surface 54 does not directly engage the exhaust pipe 46 when the sensor 10a is mounted for use.

The bore 26 of the housing 14 is sized to receive and support a sensor element 66 having a first end 70 that engages the housing 14 in the bore 26, and a second end 74 that extends out of and away from the end 18 of the housing 14. A seal ring (not shown) can be interposed between the bore 26 and the first end 70 to seal the interface. In the illustrated construction, the sensor element 66 is the type commonly referred to as a thimble-type element, however, those skilled in the art will understand that planar technology sensor elements can also be used. It should be noted, however, that sensors having thimble-type sensor elements are typically longer than sensors having planar technology sensor elements, and that any dimensional characteristics of the sensor 10a discussed below are intended to be taken in relation to other sensors using thimble-type sensor elements.

As best seen in FIG. 3, the illustrated sensor element 66 includes a ceramic, cup-shaped or thimble-shaped member 78, of the type commonly known and made from materials such as stabilized $ZrO_2$, CaO- and/or $Y_2O_3$-stabilized $ZrO_2$, $Al_2O_3$, Mg-spinel, and forsterite. The cup-shaped member 78 includes a closed end 82, an open end 86, an outer surface 90, and an inner surface 94. The inner surface 94 defines a chamber 98, the purpose of which will be described below.

An outer or exhaust electrode 102 of conductive and catalytically active material, such as platinum or other similar conductive and catalytically active materials, is positioned on the outer surface 90. A lead portion 106 of the exhaust electrode 102 extends along the outer surface 90 toward the open end 86 of the cup-shaped member 78 to be in electrical engagement with the bore 26 of the housing 14, thereby grounding the exhaust electrode 102 through the housing 14. The outer electrode 102 communicates with the exhaust gas stream, as is understood by those skilled in the art.

An inner or reference electrode 110 of conductive and catalytically active material is positioned on the inner surface 94 within the chamber 98. A lead portion 114 of the reference electrode 110 extends along the inner surface 94 toward the open end 86 of the cup-shaped member 78 and out of the chamber 98 along an end surface 118 defining the open end 86 of the member 78. The reference electrode 110 communicates with reference air inside the chamber 98, as is also understood by those skilled in the art.

The sensor 10a further includes a sleeve assembly 122 connected to the end 22 of the housing 14. The sleeve assembly 122 includes a first end 126 that, in the illustrated construction, is crimped to the housing 14 at crimps 130. Of course, other joining techniques, such as welding, adhesives, brazing, soldering, and the like, can be used instead of, or in combination with the crimps 130 to join the sleeve assembly 122 and the housing 14 and/or provide a hermetic seal between the sleeve assembly 122 and the housing 14. The sleeve assembly 122 further includes a second end 134 at a distance from the housing 14 and including an opening 138, the purpose of which will be described below.

In the illustrated construction, the sleeve assembly 122 includes a metallic sleeve 142 and a non-metallic grommet 146 at least partially retained by the sleeve 142. The sleeve assembly 122 further includes a non-metallic seal bushing 147 and retaining cap 148. The sleeve 142 includes a first end 150 corresponding to the first end 126 of the sleeve assembly 122, and a second end 154 that is stepped at step 156 to define a reduced-diameter boss 158. The boss 158 receives and supports the grommet 146.

The grommet 146 illustrated in FIG. 1 is preferably made from non-porous, non-gas-permeable polytetrafluoroethylene (PTFE) or polyethyletherketone, and includes a bore 162 extending therethrough. The grommet 146 also includes a first end 164 closest to the housing 14.

The seal bushing 147 is preferably made of viton, silicon, rubber, or similar materials and abuts the end of the grommet 146 opposite the first end 164. The retaining cap 148 covers the seal bushing 147 and at least a portion of the grommet 146. A distal end 165 of the retaining cap 148 includes the opening 138. The retaining cap is made of PTFE and is configured to engage the outer surface of the grommet 146 via a toothed engagement (not shown) that substantially prevents removal of the retaining cap 148 once it has been installed on the grommet 146. It is to be understood that the illustrated sleeve assembly 122, and particularly the configuration of the second end 134 can be modified depending on the specific type of grommet 146, seal bushing 147, and retaining cap 148 used.

The sleeve assembly 122 houses and protects additional components of the sensor 10a. A ceramic bushing 166 is disposed within the sleeve assembly 122 and includes a first end 170 received in the bore 26 of the housing 14, a second end 174 at least partially received in the boss 158 of the sleeve 142, a stepped portion 178 adjacent the second end 174, and a bore 182 extending through the bushing 166 between the first and second ends 170, 174. A disk spring 186 is disposed between the sleeve 142 and the stepped portion 178 of the bushing 166 to bias the bushing 166 toward the housing 14. In the illustrated construction, the bushing 166 is made of ceramic materials known as soapstone steatite or crypto-crystalline talc, and in some instances, can be made from materials having lower thermal conductivity and higher compressive strength, such as DOT-HERM DT600M available from Industria Engineering Products in Uxbridge, United Kingdom.

The bore 182 of the bushing 166 houses a conductive contact pin assembly 190 that electrically connects the sensor element 66 to a wire lead 194 extending from the sensor 10a for electrical connection to the engine control unit (ECU). The bushing 166 thereby electrically isolates the contact pin assembly 190 from the housing 14 and the sleeve 142. As shown in FIGS. 1 and 4, and with reference to FIG. 3, the contact pin assembly 190 includes a first portion 196 defining a base, or substantially planar plate portion 198, and an annular body portion, or stem 206 extending from the plate portion 198. The plate portion 198 engages the end surface 118 of the cup-shaped member 78, thereby electrically contacting the lead portion 114 of the reference electrode 110. In the illustrated construction, the first portion 196 is a deep-drawn part. The biasing of the bushing 166 toward the housing 14 by the disk spring 186 helps maintain the electrical connection between the plate portion 198 and the lead portion 114.

The contact pin assembly 190 also includes an annular second portion 202, which upon initial connection with the first portion 196, is slidably movable inside and in telescoping relation with, the stem 206 to establish an overall length "L" (see FIG. 4) of the contact pin assembly 190. As shown in FIGS. 1 and 4, the second portion 202 is a hollow tube.

To assemble the first and second portions 196, 202, the second portion 202 is placed in telescoping relation with the first portion 196, adjusted relative to the first portion 196 to achieve the desired overall length L of the contact pin assembly 190, and secured to the first portion. As shown in FIGS. 1 and 4, the first and second portions 196, 202 are secured together by spot-welding, however, other joining techniques such as brazing, crimping, adhesive bonding, and so forth may be used to secure together the first and second portions 196, 202.

Figure 5:
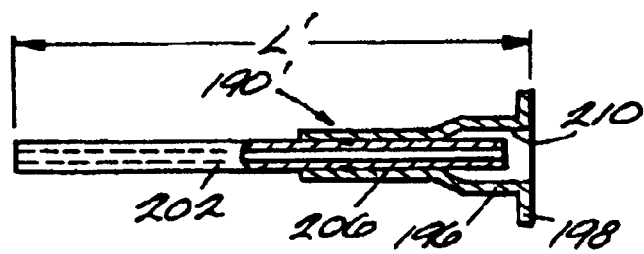
FIG. 5 is a cross-sectional view of the contact pin assembly of FIGS. 1 and 2 shown in the second configuration.

FIGS. 4 and 5 illustrate contact pin assemblies 190, 190' assembled in a first configuration and a second configuration, respectively. The first configuration of the contact pin assembly 190, as illustrated in FIG. 4, has an overall length L and is utilized in sensor 10a (FIG. 1). The second configuration of the contact pin assembly 190', as illustrated in FIG. 5, has a shorter overall length L' and is utilized in sensor 10a' (FIG. 2). In the second configuration of the contact pin assembly 190', the second portion 202 is inserted further into the stem 206 as compared to the same components in the first configuration of the contact pin assembly 190. The overall length L of the contact pin assemblies 190, 190' is determined by lengths L1 and L2 of the sensors 10a, 10a', discussed in more detail below.

It should be noted that FIGS. 4 and 5 illustrate bow the same components (the first portion 196 and the second portion 202) are used to form contact pin assemblies 190, 190' of different configurations having different overall lengths L, L', respectively. This reduces the number of different parts needed to manufacture sensors of different lengths. Those skilled in the art will understand that the first and second portions 196, 202 can be assembled in a virtually infinite number of overall lengths. Those skilled in the art will also understand that modifications can be made to the first and/or second portions 196, 202 to facilitate assembly when a large number of sensors of a predetermined length are being made.

Figure 6:
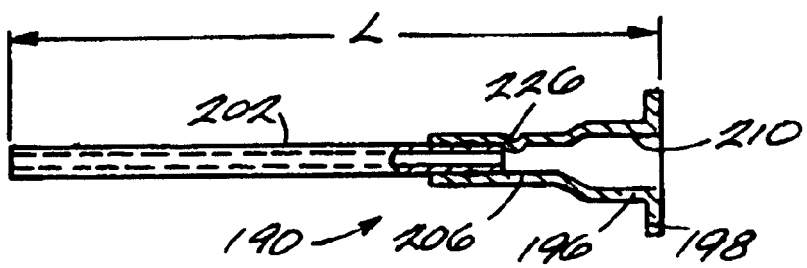
FIG. 6 is a cross-sectional view of the contact pin assembly of FIGS. 4 and 5 shown with a dimple for facilitating assembly.

For example, as shown in FIG. 6, the first portion 196 can include a locating feature, such as an indentation 226 in the stem 206, to locate the end of the second portion 202 inserted into the stem 206. The indentation 226 may alternatively be positioned at other locations along the stem 206 for different length contact pin assemblies 190. Further, different first portions 196 having different indentation locations may be available during assembly so that contact pin assemblies 190 of different overall lengths can be readily assembled.

The second portion 202 extends through the bore 162 of the grommet 146. Therefore, the grommet 146 electrically isolates the contact pin assembly 190 from the sleeve 142. An end of the wire lead 194 is inserted and crimped or otherwise electrically and mechanically secured into the hollow second portion 202 of the contact pin assembly 190, thereby completing the electrical pathway between the sensor element 66 and the wire lead 194. The wire lead 194 exits the sleeve assembly 122 through the opening 138 in the retaining cap 148. The seal bushing 147 and the retaining cap 148 substantially seal the end of the sensor 10a around the contact pin assembly 190/wire lead 194 interface.

The first and second portions 196, 202 provide a pathway for reference air to enter and exit the chamber 98 defined by the cup-shaped member 78. Reference air from the atmosphere enters the chamber 98 through the wire lead 194. More specifically, the wire lead 194 typically includes a plurality of wire strands braided together to form the conductive portion of the wire lead 194. Reference air flows in and around the braided strands, and is channeled to the chamber 98 by the tubular second portion 202 and the stem 206. The reference air flows into the stem 206 around the spot welds and through the second portion 202. An aperture 210 in the plate portion 198 provides communication between the chamber 98 and the stem 206. A series of apertures, slits, louvers, or "fish-gills" (not shown) may also be formed in the stem 206 to allow reference air surrounding the exterior of the stem 206 to enter the chamber 98 through the wall of the stem 206 and through the aperture 210.

The sensor 10a also includes a tube 214 that substantially surrounds and protects the second end 74 of the sensor element 66 extending into the exhaust gas stream. The illustrated tube 214 is made of stainless steel or other heat resistant metal alloy and includes a first, open end 218 configured to be secured to the housing 14 by the crimp shoulder 30. Alternatively, the open end 218 can be welded to the housing 14. A second, closed end 222 of the tube substantially surrounds and protects the second end 74 of the sensor element 66. The tube 214 allows exhaust gas to enter therein for communication with the sensor element 66, yet protects the sensor element 66 from debris particles contained within the exhaust gas stream.

The sensor 10a of FIG. 1 is well suited for use in non-automotive applications, such as motorcycles, snowmobiles, ATV's, lawnmowers, and the like because of the various length dimensions that can be achieved depending on the specific application in which the sensor 10a will be used. Because internal combustion engines in non-automotive applications are typically smaller, less confined, and do not generate as much heat as automotive engines, it is possible to reduce the overall length of the sensor 10a from that of prior art sensors previously used in the automotive industry.

For example, the sensor 10a includes a first length dimension L1 defined as a distance from the second end surface 54 of the nut portion 38 to the second end 134 of the sleeve assembly 122. The first length dimension L1 of the sensor 10a can range from about 39 mm to about 59 mm, and even more preferably from about 39 mm to about 55 mm. One preferred construction of the sensor 10a has a first length dimension L1 of about 43 mm. This range is believed to provide at least some length dimensions L1 that are shorter than corresponding lengths of prior art exhaust gas sensors (believed to go only as low as 56 mm for prior art thimble-type sensors), making the sensor 10a well-suited for the confined spaces of smaller, non-automotive engine applications.

The sensor 10a also includes a second length dimension L2 defined as a distance from the second end surface 54 of the nut portion 38 to the step 156 in the sleeve 142, which is closely adjacent to or substantially co-planar with the first end 164 of the grommet 146. The second length dimension L2 of the sensor 10a can range from about 15 mm to about 45 mm, and even more preferably from about 15 mm to about 35 mm. One preferred construction of the sensor 10a has a second length dimension L2 of about 19 mm. This range is believed to provide at least some length dimensions L2 that are shorter than corresponding lengths of prior art exhaust gas sensors, again making the sensor 10a well-suited for the confined spaces of smaller, non-automotive engine applications.

FIG. 2 illustrates a sensor 10a' that is substantially the same as the sensor 10a, but that is significantly shorter in overall length. The shortening of the first and second length dimensions L1 and L2 is achieved by shortening various components of the sensor 10a. The shortened components are indicated as prime ('). More specifically, as seen in FIG. 2, the bushing 166' and the sleeve 142' are shortened in length to achieve the shorter length dimensions L1 and L2. However, the same first and second portions 196, 202 used in the sensor 10a may also be used in the shortened sensor 10a'. For this to occur, the second portion 202 is inserted further into the first portion 196 (see FIG. 5) before securing together the portions 196, 202. The remaining components not labeled in FIG. 2 are substantially identical to those referenced in FIG. 1.

The ability to shorten and lengthen the dimensions L1 and L2 within the ranges noted above is largely dictated by the operating temperature observed by the sensors 10a, 10a' for the particular application, and the specific materials being used in the sensor components. More specifically, the acceptable minimum length for a given sensor 10a, 10a' is based mainly on the rated maximum continuous operating temperature of the sealing grommet 146 being used, and the sensor's ability to dissipate enough heat along its length so that the rated operating temperature of the grommet 146 is not exceeded.

Figure 22:
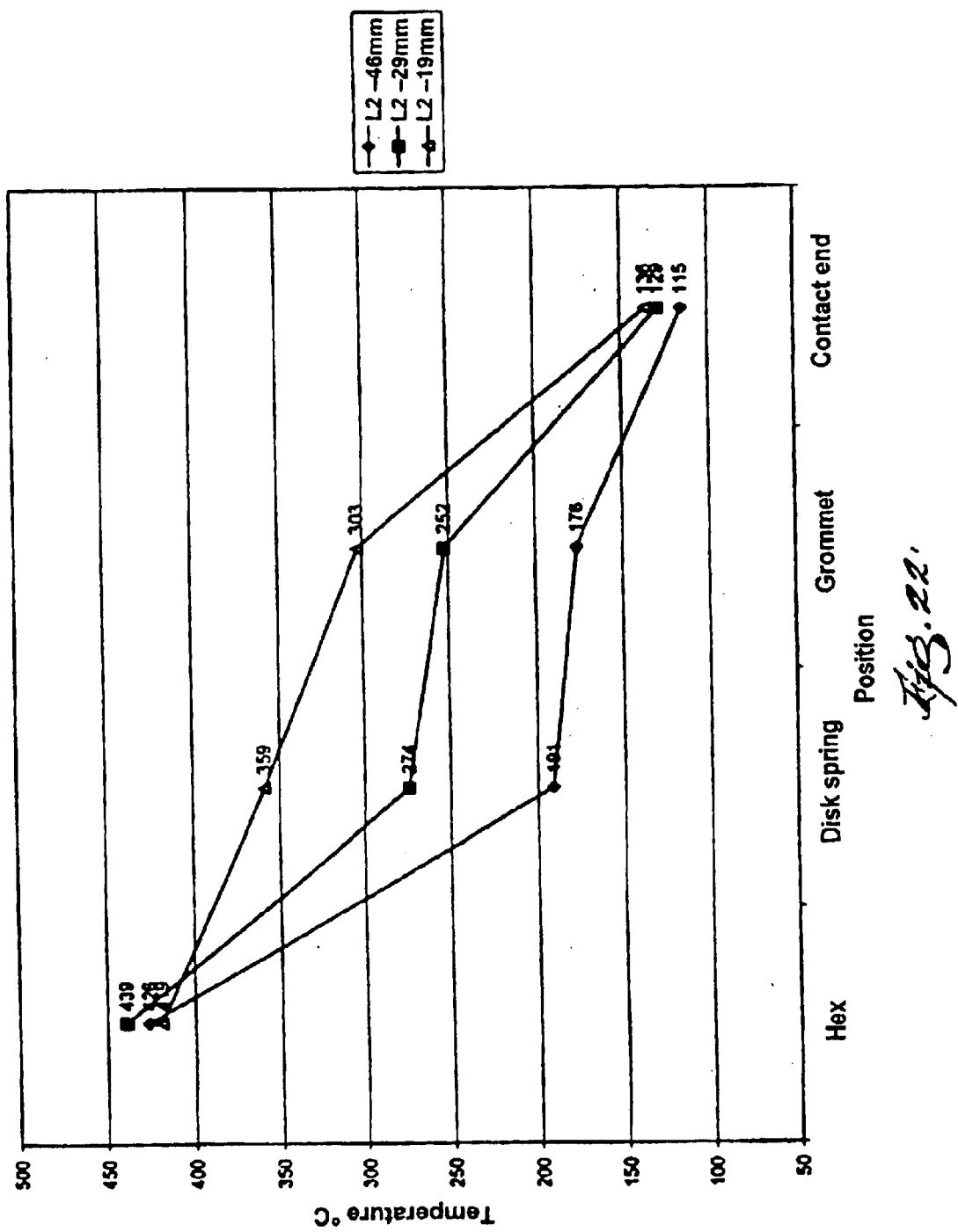
FIG. 22 is a graph illustrating the measured temperature at various points along the length of an exhaust gas sensor for three sensors of differing body length.

For example, FIG. 21 illustrates a graph of the minimum second length dimension L2 (labeled as body length), as a function of the temperature of the hex or nut portion 38. The two data sets were modeled for sensors 10a, 10a' with grommets 146 rated for maximum continuous temperatures of 250 (PTFE) and 300 (polyethyletherketone) degrees Centigrade. Using this model, a designer can determine the approximate minimum body length L2 of the sensor 10a, 10a' for any given application based on the maximum temperature the sensor 10a, 10a' will face, understanding that each installation will have variations in gas temperature, flow, and exhaust pipe installation detail that will impact the minimum length L2. FIG. 22 illustrates another model illustrating temperature distribution over the components of the sensors 10a, 10a' for varying second length dimensions L2.

To facilitate shortening the sensors 10a, 10a', heat-dissipating features can be added to the sensor 10a, 10a'. For example, fins (not shown) can be added to the tube 214 and/or the nut portion 38 of the housing 14. Additionally, holes (not shown) can be drilled in the nut portion 38 to increase surface area for heat radiation. As mentioned above, DOTHERM DT600M can be used as the material for the bushing 166 and polyethyletherketone can be used as the material for the grommet 146. High temperature resistant metals can be used for the sleeve 142, and the thickness of the sleeve 142 can be varied.

The sensor 10a further includes a third length dimension L3 defined as a distance from the second end 222 of the tube 214 to the second end surface 54 of the nut portion 38. The third length dimension L3 can range from about 18 mm to about 28 mm, and even more preferably from about 23 mm to about 28 mm. Because the exhaust pipes in non-automotive applications are typically smaller, reducing the third length dimension L3 will not negatively impact the gas flow to the sensor element 66. The same sensor element 66 can be used over this entire range of L3 dimensions by modifying the bore 26 in the housing 14 to vary the seating position of the sensor element 66. A corresponding change in the length of the bushing 166, 166' and/or the sleeve 142, 142' may also be needed.

The specific configuration of the contact pin assemblies 190, 190' illustrated in FIGS. 1–2 and 4–5 are only two of many suitable contact pin configurations that can be used. Those skilled in the art will recognize that the configuration of the contact pin assemblies 190, 190' can be modified without departing from the invention.

With reference to FIG. 7, a second contact pin assembly 290 is shown being utilized in a sensor 10b. With the exception of the contact pin assembly 290, the other components of the sensor 10b are the same as those described with reference to the sensor 10a of FIG. 1.

Figure 9:
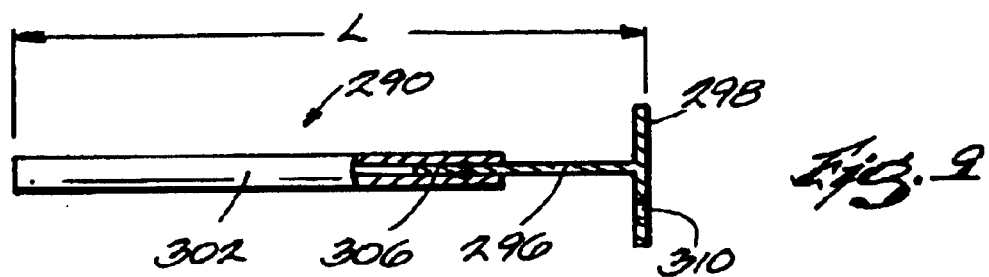
FIG. 9 is a cross-sectional view of the second contact pin assembly of FIGS. 7 and 8 shown in the first configuration.

As seen in FIGS. 7 and 9, the contact pin assembly 290 includes a first portion 296 defining a base, or substantially planar plate portion 298, and a solid stem 306 extending from the plate portion 298. The plate portion 298 engages the end surface 118 of the cup-shaped member 78, thereby electrically contacting the lead portion 114 of the reference electrode 110. In the illustrated construction, the first portion 296 is a cold-headed part.

The contact pin assembly 290 also includes an annular second portion 302, which upon initial connection with the first portion 296, is slidably movable on, and in telescoping relation with, the stem 306 to establish an overall length "L" (see FIG. 9) of the contact pin assembly 290. As shown in FIGS. 7 and 9, the second portion 302 is a hollow tube sized to fit over the stem 306. Similar methods of assembling the first and second portions 296, 302 may be utilized as described above with the first and second portions 196, 202 of the contact pin assembly 190.

Figure 10:
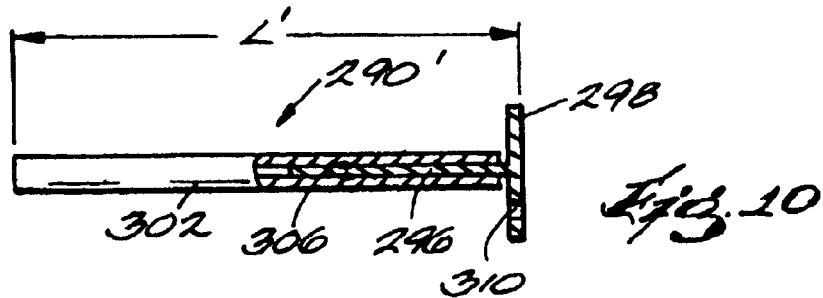
FIG. 10 is a cross-sectional view of the second contact pin assembly of FIGS. 7 and 8 shown in the second configuration.

FIGS. 9 and 10 illustrate contact pin assemblies 290, 290' assembled in a first configuration and a second configuration, respectively. The first configuration of the contact pin assembly 290, as illustrated in FIG. 9, has an overall length L and is utilized in sensor 10b. The second configuration of the contact pin assembly 290', as illustrated in FIG. 10, has a shorter overall length L' and is utilized in sensor 10b'. In the second configuration of the contact pin assembly 290', the second portion 302 is inserted further onto the stem 306 as compared to the same components in the first configuration of the contact pin assembly 290. The overall length of the contact pin assemblies 290, 290' is determined by lengths L1 and L2 of the sensors 10b, 10b', as previously discussed above.

It should be noted that FIGS. 9 and 10 illustrate how the same components (the first portion 296 and the second portion 302) are used to form contact pin assemblies 290, 290' of different configurations having different overall lengths, L, L', respectively. This reduces the number of different parts needed to manufacture sensors of different lengths. Those skilled in the art will understand that the first and second portions 296, 302 can be assembled in a virtually infinite number of overall lengths. Those skilled in the art will also understand that modifications can be made to the first and/or second portions 296, 302 to facilitate assembly when a large number of sensors of a predetermined length are being made.

Figure 11:
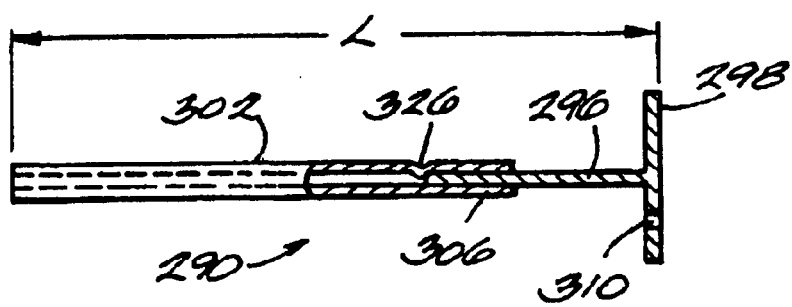
FIG. 11 is a cross-sectional view of the second contact pin assembly of FIGS. 7 and 8 shown with a dimple for facilitating assembly.

For example, as shown in FIG. 11, the second portion 302 can include a locating feature, such as an indentation 326, to locate the end of the stem 306 when the stem 306 is inserted into the second portion 302. The indentation 326 facilitates assembly of the contact pin assembly 290 since the overall length L of the contact pin assembly 290 is defined by the location of the indentation 326 in the second portion 302. By providing the indentation 326 in the second portion 302, two different contact pin assembly lengths are possible depending on which end of the second portion 302 is engaged onto the stem 306. The contact pin assembly 290 defines a shorter length when the opposite end of the second portion 302 is engaged onto the stem 306. The indentation 326 may alternatively be positioned at other locations along the second portion 302 to yield contact pin assemblies 290 of different overall lengths. Further, different second portions 302 having different indentation locations may be available during assembly so that contact pin assemblies 290 of different overall lengths can be readily assembled.

The first and second portions 296, 302 provide a pathway for reference air to enter and exit the chamber 98 defined by the cup-shaped member 78. Reference air from the atmosphere enters the chamber 98 through the wire lead 194 as described above. Reference air is then channeled through the tubular second portion 302, around the stem 306, past the welds securing the stem 306 to the second portion 302, and into the space defined by the bore 182. An aperture 310 in the plate portion 298 provides communication between the chamber 98 and the bore 182.

Figure 15:
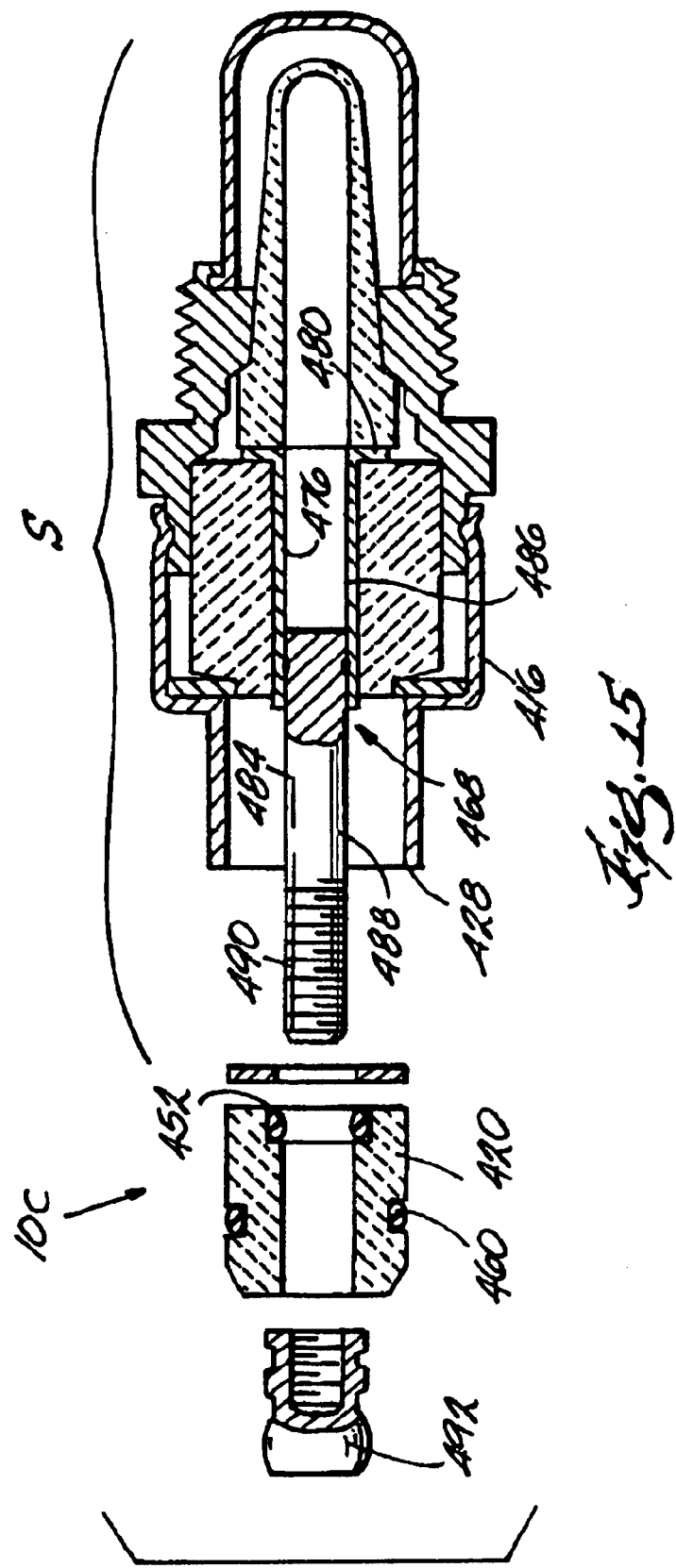
FIG. 15 is an exploded cross-sectional view of the sensor of FIG. 12.
Figure 11:
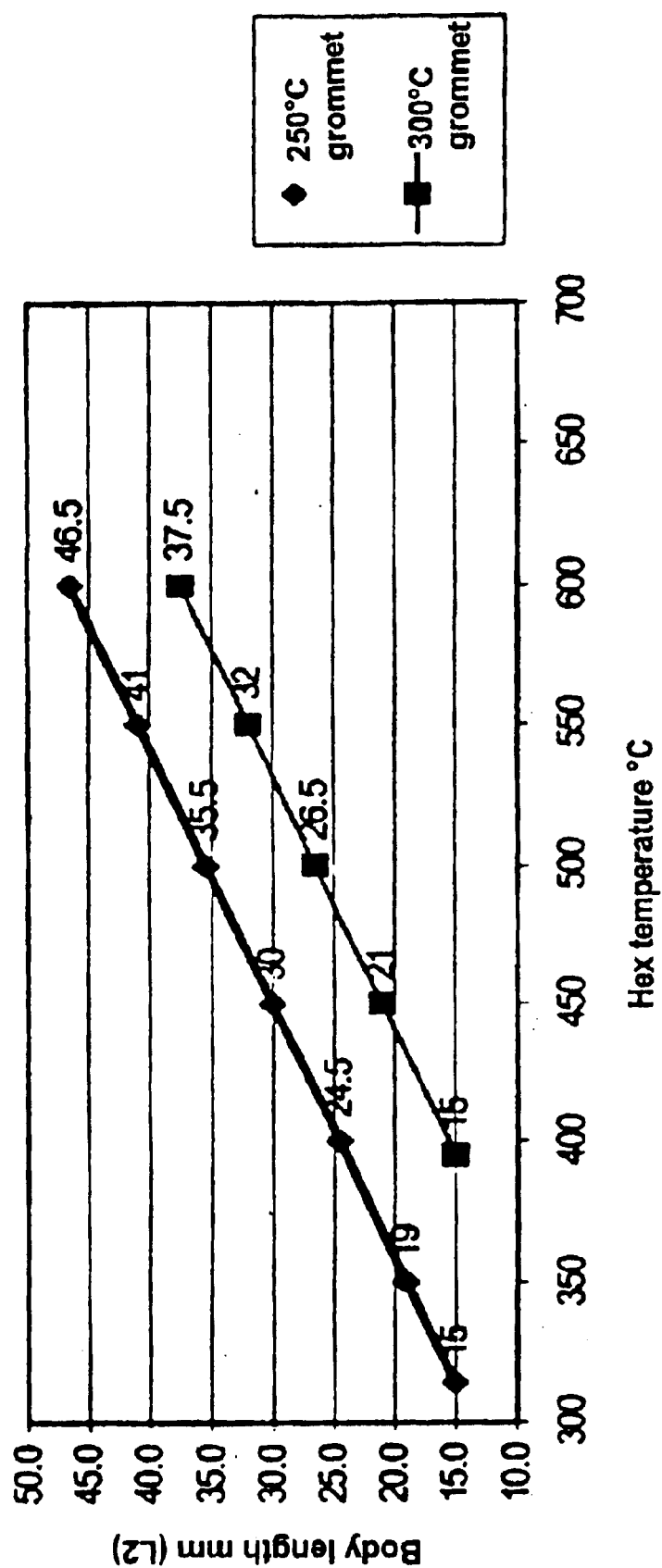

FIGS. 12 and 15 illustrate a sensor 10c of another construction. Components of the sensor 10c that are substantially the same as components of the sensors 10a, 10a', 10b, 10b' have been given like reference numerals and will not be discussed again in detail. Like the sensors 10a, 10a', 10b, 10b', the sensor 10c is also well suited for non-automotive applications, such as motorcycles, snowmobiles, ATV's, lawnmowers, and the like.

The sensor 10c includes a sleeve assembly 400 that is configured differently from the sleeve assembly 122 of the sensors 10a, 10a', 10b, 10b'. Specifically, the sleeve assembly 400 includes a first end 404 that, in the illustrated construction, is crimped to the housing 14 at crimps 130. Of course, other joining techniques, such as welding, adhesives, brazing, soldering, and the like, can be used instead of, or in combination with the crimps 130 to join the sleeve assembly 400 and the housing 14 and/or to provide a hermetic seal between the sleeve assembly 400 and the housing 14. The sleeve assembly 400 further includes a second end 408 at a distance from the housing 14 and including an opening 412, the purpose of which will be described below.

As shown in FIG. 12, the sleeve assembly 400 includes a metallic sleeve 416 and a non-metallic grommet 420 at least partially retained by the sleeve 416 to define at least a portion of the second end 408 of the sleeve assembly 400. The sleeve 416 includes a first end 424 corresponding to the first end 404 of the sleeve assembly 400, and a second open end 428 sized to receive the grommet 420. The sleeve 416 is stepped at step 432 to receive and support the grommet 420.

The grommet 420 illustrated in FIGS. 12 and 13 is preferably made from porous, gas-permeable polytetrafluoroethylene (PTFE), for reasons that will be discussed below. The grommet 420 has a first end 436 closest to the housing 14 and a second end 440 at a distance from the first end 436. The grommet 420 includes a bore 444 extending therethrough between the ends 436, 440. An end of the bore 444 adjacent the end 440 defines the opening 412. An end of the bore 444 adjacent the end 436 includes a larger diameter portion 448 configured to receive an O-ring 452 or similar sealing device, the purpose of which will be described below.

The outer surface 456 of the grommet 420 includes a groove 458 configured to receive an O-ring 460 or similar sealing device that substantially seals the interface between the outer surface 456 of the grommet 420 and an inner wall 464 of the sleeve 416, to substantially prevent the leakage of liquids into the sensor element 66. It is to be understood that the illustrated sleeve assembly 400, and particularly the configuration of the second end 408 can be modified depending on the specific type and configuration of grommet 420 used.

The ceramic bushing 166c of the sensor 10c is similar to the bushing 166, except that the second end 174c has been shortened due to the lack of any boss in the sleeve 416. The bore 182c of the bushing 166c houses a conductive contact pin assembly 468 that electrically connects the sensor element 66 to a connector 472 for electrical connection to the engine control unit (ECU). The contact pin assembly 468 includes a first portion 476 defining a base, or substantially planar plate portion 480, and an annular body portion, or stem 486 extending from the plate portion 480. The plate portion 480 engages the end surface 118 of the cup-shaped member 78, thereby electrically contacting the lead portion 114 of the reference electrode 110. In the illustrated construction, the first portion 476 is a deep-drawn part.

Figure 14:
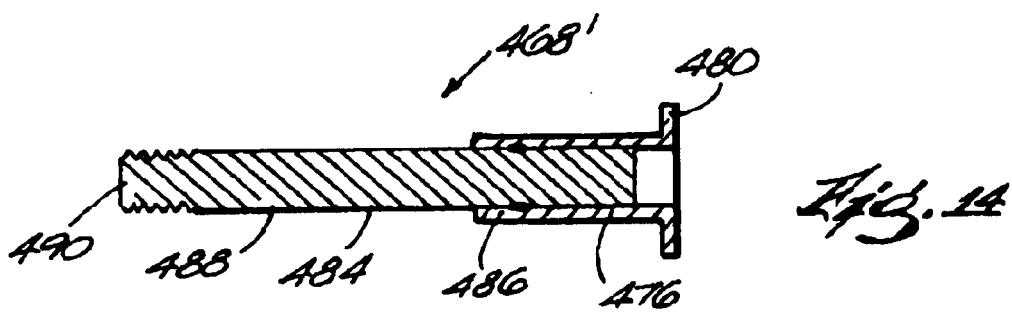
FIG. 14 is a cross-sectional view of the third contact pin assembly of FIGS. 12 and 13 shown in the second configuration.

The contact pin assembly 468 also includes a solid second portion 484, which upon initial connection with the first portion 476, is slidably movable inside, and in telescoping relation with, the stem 486 to establish an overall length of the contact pin assembly 468. As shown in FIGS. 12 and 14, the second portion is a solid rod. Similar methods of assembling the first and second portions 476, 484 may be utilized as described above with the first and second portions 196, 202 of the contact pin assembly 190 and the first and second portions 296, 302 of the contact pin assembly 290. Either of the first or second portions 476, 484 may include locating features (not shown) that would facilitate assembly of the first and second portions 476, 484 into a contact pin assembly 468 having a specified overall length.

The second portion 484 extends through the bore 444 of the grommet 420 and exits the sleeve assembly 400 through the opening 412. The grommet 420 thereby electrically isolates a portion of the contact pin assembly 468 from the sleeve 416. The O-ring 452 substantially seals the interface between the bore 444 of the grommet 420 and an outer surface 488 of the second portion 484 to substantially prevent the leakage of liquids into the sensor element 66.

The second portion 484 of the contact pin assembly 468 further includes a threaded portion 490 that receives a metallic spark plug-type post terminal 492. As used herein and in the appended claims, the term "spark plug-type post terminal" means any terminal of the type commonly configured for use on a spark plug. Preferably, the spark plug-type post terminal 492 conforms with the Society of Automotive Engineers (SAE) J548-1 standards for spark plugs, however, other non-conforming terminal designs can also be used.

The spark plug-type post terminal 492 is internally threaded for receipt onto the threaded portion 490 of the second portion 484, thereby becoming electrically interconnected with the contact pin assembly 468 to complete the electrical pathway between the sensor element 66 and the connector 472. A bulbous end 496 of the spark plug-type post terminal 492 is configured to be received in the connector 472 in the same manner commonly known for pressing a similar connector onto a spark plug post terminal. Additionally, threading the spark plug-type post terminal 492 onto the second portion 484 mechanically secures and retains the grommet 420 and the O-rings 452, 460 in the second end 428 of the sleeve 416. The end 440 of the grommet 420 extends axially beyond the end 428 of the sleeve 416 to prevent the spark plug-type post terminal 492 and the connector 472 from contacting the sleeve 416 and grounding out the sensor element 66.

The electrical connection of the sensor 10c using the spark plug-type post terminal 492 and the connector 472 eliminates the lead wire air exchange path to the chamber 98 that was described above with respect to the sensors 10a, 10a', 10b, 10b'. Therefore, a different way of providing reference air exchange to the chamber 98 of the sensor 10c is provided. Specifically, the grommet 420 is made of a porous, gas-permeable PTFE material that allows air to pass through the grommet 420, while preventing liquids from passing therethrough. The reference air is therefore able to enter the sleeve assembly 400, flow around and/or through the bushing 166c, around the plate portion 480 and into the chamber 98. Also, the reference air may enter the sleeve assembly 400, flow into the tubular first portion 476 past the spot-welded connection between the first and second portions 476, 484, and into the chamber 98.

Using the spark plug-type post terminal 492 and the connector 472 eliminates the need for platform-specific or application-specific wiring harnesses, and provides a uniform connection that can be introduced and used across all platforms and applications. The uniformity provided by the spark plug-type post terminal 492 makes the sensor 10c, and other sensors that use the spark plug-type post terminal 492 and connector 472 arrangement, quickly and easily replaceable and interchangeable with aftermarket replacement sensors having a spark plug-type post terminal 492. It should be understood that the invention, as it pertains to the use of the spark plug-type post terminal 492 and connector 472 arrangement, is not limited to the illustrated sensor 10c, but can be used on any existing or new sensor to provide a new and improved form of electrical connection between the sensor element (thimble-type, planar, or otherwise) and the ECU. This includes sensors used for both automotive and non-automotive applications.

In addition to providing uniformity of sensor connections, the spark plug-type post terminal 492 also provides benefits in testing and assembling the sensor 10c. It is known to perform high temperature testing on longer exhaust gas sensors used for automotive applications, prior to shipping the sensors to a customer. Typically, the sensor element end of a sensor is tested in a high gas temperature environment (e.g., about 850° to 1050° C.) to ensure the sensor is operating properly. Using these standardized tests for the shortened sensors 10a', 10b' could be problematic, in that the grommet 146 may not be able to withstand the high testing temperatures, since less sensor body length is available to dissipate heat.

The construction of the sensor 10c provides a way that the sensor 10c can be tested using existing standardized temperature testing procedures and equipment, without jeopardizing the components of the sensor 10c not suited to undergo such testing. Specifically, as seen in FIG. 15, the sensor 10c can be initially assembled into a subassembly (indicated generally by the letter S) that is fully functional and capable of operating as an exhaust gas sensor. The components of the subassembly S are capable of withstanding the predetermined temperatures associated with the standardized testing, and an electrical connection can be made directly to the threaded portion 490 of the second portion 484 using a temporary clip-on connector (not shown).

The components not suited for undergoing the high temperature testing, namely the grommet 420 and the O-rings 452, 460 in the illustrated construction, are left off the subassembly S during high temperature testing. After the testing is completed, the grommet 420 and O-rings 452, 460 are inserted into the second end 428 of the sleeve 416 and over the threaded portion 490 of the second portion 484. Next, the spark plug-type post terminal 492 is threaded onto the threaded portion 490 of the second portion 484 to mechanically secure the grommet 420 and the O-rings 452, 460 to the subassembly S, as described above. This construction therefore allows shorter sensors to be tested using the standardized temperature testing procedures and equipment already in place for longer exhaust gas sensors of the type used in automotive applications.

The sensor 10c also includes a first length dimension L1 defined as a distance from the second end surface 54 of the nut portion 38 to the second end 408 of the sleeve assembly 400. The first length dimension L1 of the sensor 10c can range from about 33 mm to about 60 mm, and even more preferably from about 33 mm to about 55 mm. One preferred construction of the sensor 10c has a first length dimension L1 of about 33 mm. Again, this range is believed to provide at least some length dimensions L1 that are lower than corresponding lengths of prior art exhaust gas sensors (believed to go only as low as 56 mm for prior art thimble-type sensors), making the sensor 10c well-suited for the confined spaces of smaller, non-automotive engine applications.

The sensor 10c also includes a second length dimension L2 defined as a distance from the second end surface 54 of the nut portion 38 to the step 432 in the sleeve 416, which is closely adjacent to or substantially co-planar with the first end 436 of the grommet 420. The second length dimension L2 of the sensor 10c can range from about 19 mm to about 46 mm, and even more preferably from about 19 mm to about 41 mm. One preferred construction of the sensor 10c has a second length dimension L2 of about 19 mm. This range is believed to provide at least some length dimensions L2 that are lower than corresponding lengths of prior art exhaust gas sensors, again making the sensor 10c well-suited for the confined spaces of smaller, non-automotive engine applications.

FIG. 13 illustrates a sensor 10c' that is substantially the same as the sensor 10c, but that is significantly shorter in overall length. The shortening of the first and second length dimensions L1 and L2 is achieved by shortening various components of the sensor 10c. More specifically, as seen in FIG. 13, the bushing 166c', and the sleeve 416c' are shortened in length to achieve shorter length dimensions L1 and L2. However, the same first and second portions 476, 484 used in sensor 10c may also be used in the shortened sensor 10c' to form a shortened contact pin assembly 468' (shown separately in FIG. 14). For this to occur, the second portion 484 is inserted further into the stem 486 before securing together the portions 476, 484. The remaining components not labeled in FIG. 13 are substantially identical to those referenced in FIG. 12.

The sensors 10c, 10c' further include a third length dimension L3 that is the same as discussed above for the sensors 10a, 10a', 10b, 10b'. As with the sensors 10a, 10a', 10b, 10b', the same sensor element 66 can be used over this entire range of L3 dimensions by modifying the bore 26 in the housing 14 to vary the seating position of the sensor element 66. A corresponding change in the length of the bushing 166c, 166c' and/or contact pin assembly 468, 468' and/or sleeve 416, 416c' may also be needed.

With reference to FIG. 16; a fourth contact pin assembly 568 is shown being utilized in a sensor 10d. With the exception of the contact pin assembly 568, the other components of the sensor 10d are the same as those described with reference to the sensor 10c of FIG. 12.

The contact pin assembly 568 (shown separately in FIG. 18) electrically connects the sensor element 66 to the connector 472 for electrical connection to the engine control unit (ECU). The contact pin assembly 568 includes a first portion 576 defining a base, or a substantially planar plate portion 580, and a solid stem 586 extending from the plate portion 580. The plate portion 580 engages the end surface 118 of the cup-shaped member 78, thereby electrically contacting the lead portion 114 of the reference electrode 110. In the illustrated construction, the first portion 576 is a cold-headed part.

Figure 18:
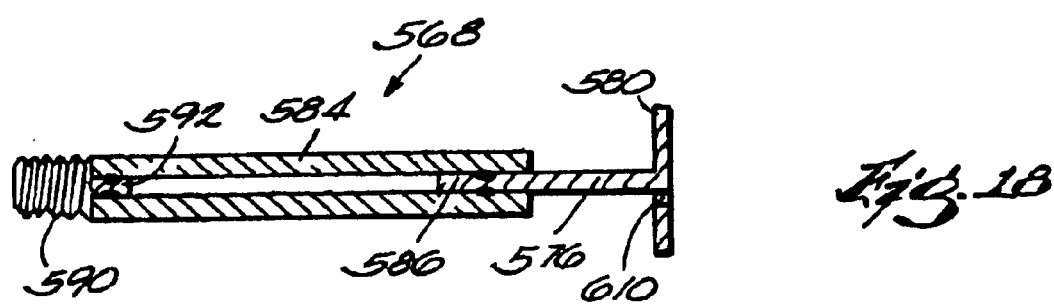
FIG. 18 is a cross-sectional view of the fourth contact pin assembly of FIGS. 16 and 17 shown in the first configuration.

The contact pin assembly 568 also includes an annular second portion 584, which upon initial connection with the first portion 576, is slidably movable on and in telescoping relation with, the stem 586 to establish an overall length of the contact pin assembly 568. As shown in FIGS. 16 and 18, the second portion 584 is a hollow tube. Similar methods of assembling the first and second portions 576, 584 may be utilized as described above with the first and second portions 476, 484 of the contact pin assembly 468, the first and second portions 296, 302 of the contact pin assembly 290, or the first and second portions 196, 202 of the contact pin assembly 190. Either of the first or second portions 576, 584 may include locating features (not shown) that would facilitate assembly of the first and second portions 576, 584 into a contact pin assembly 568 having a specified overall length.

The second portion 584 extends through the bore 444 of the grommet 420 and exits the sleeve assembly 400 through the opening 412. A threaded insert 590 includes a stem portion 592 sized to be received and secured in an end of the tubular second portion 584. The threaded insert 590 receives the metallic spark plug-type post terminal 492 in the manner described above for the second portion 484.

Reference air enters the sleeve assembly 400 through the grommet 420, flows around and/or through the bushing 166c, around the plate portion 580 and into the chamber 98. Additionally, the reference air may enter the chamber 98 through an aperture 610 in the plate portion 580.

FIG. 17 illustrates a sensor 10d' that is substantially the same as the sensor 10d, but that is significantly shorter in overall length. The shortening of the first and second length dimensions L1 and L2 is achieved by shortening various components of the sensor 10d. More specifically, as seen in FIG. 17, the bushing 166c', and the sleeve 416c' are shortened in length to achieve shorter length dimensions L1 and L2. However, the same first and second portions 576, 584 used in the sensor 10d may also be used in the shortened sensor 10d'. For this to occur, the second portion 584 is inserted further onto the stem 586 of the first portion 576 before securing together the portions 576, 584. The remaining components not labeled in FIG. 17 are substantially identical to those referenced in FIG. 16.

FIG. 19 illustrates a sensor 10e of yet another construction. An adjustable contact pin assembly 668 is shown being utilized with a heated exhaust gas sensor 10e. The sensor 10e utilizes a heating element 672 for pre-heating the reference air in the chamber 98 of the sensor 10e. The heated exhaust gas sensor 10e, with the exception of the contact pin assembly 668, is of a known construction and will not be described in detail.

The contact pin assembly 668 includes a first portion 676 defining a base, or a substantially planar plate portion 680, and an annular stem 686 extending from the plate portion 680. The plate portion 680 engages the end surface of the cup-shaped member, thereby electrically contacting the lead portion of the reference electrode. The plate portion also includes an aperture 690 for receiving the heating element 672.

The contact pin assembly 668 also includes a solid second potion 684, which upon initial connection with the first portion 676, is slidably movable inside, and in telescoping relation with, the stem 686 to establish a specified overall length of the contact pin assembly 668. As shown in FIGS. 19 and 20, the second portion 684 is a solid pin or rod. Similar methods of assembling the first and second portions 676, 684 may be utilized as described above with the components of the contact pin assemblies 190, 290, 468, 568. Also, either of the first or second portions 676, 684 may include locating features (not shown) that would facilitate assembly of the first and second portions 676, 684 into a contact pin assembly 668 having a specified overall length.

To shorten or lengthen the sensor 10e, various components of the sensor 10e may be shortened or lengthened accordingly. However, the same first and second portions 676, 684 used in the sensor 10e may also be used in either a shortened sensor (not shown) or a lengthened sensor (not shown). For this to occur, the second portion 684 is inserted further into the stem 686 (to shorten the sensor 10e), or the second portion 684 is extended further from the stem 686 (to lengthen the sensor 10e).

Other features and advantages of the invention will become apparent to those skilled in the art upon review of the following detailed description, claims, and drawings.

I claim:

1. A contact pin assembly for an exhaust gas sensor having a sensor element, the contact pin assembly comprising:
   a first portion configured to be electrically connected to the sensor element when the contact pin assembly is installed in the exhaust gas sensor; and
   a second portion configured to be connected to the first portion in either of a first configuration, wherein the contact pin assembly has a first overall length, or a second configuration, wherein the contact pin assembly has a second overall length less than the first overall length.

2. The contact pin assembly of claim 1, wherein the second portion is configured to be connected to the first portion in more than two configurations.

3. The contact pin assembly of claim 1, wherein the first and second portions are configured to be positioned in telescoping relation with respect to one another.

4. The contact pin assembly of claim 1, wherein the first and second portions are slidably movable with respect to one another between the first configuration and the second configuration.

5. The contact pin assembly of claim 1, wherein the first portion includes a base configured to engage the sensor element and a stem extending from the base, and wherein the second portion defines a tube configured to be received over at least a portion of the stem.

6. The contact pin assembly of claim 5, wherein the second portion further includes an insert having a first end received in the tube and a second end extending from the tube and being threaded to receive a spark-plug type post terminal.

7. The contact pin assembly of claim 1, wherein the first portion includes a base configured to engage the sensor element and at least a partially hollow stem extending from the base, and wherein the second portion is at least partially received inside the hollow stem.

8. The contact pin assembly of claim 7, wherein the second portion defines a tube that is at least partially received inside the hollow stem.

9. The contact pin assembly of claim 7, wherein the second portion defines a solid rod having a first end received inside the hollow stem and a threaded second end to receive a spark-plug type post terminal.

10. The contact pin assembly of claim 1, wherein the first portion includes an aperture sized to receive a heater.

11. The contact pin assembly of claim 1, wherein at least one of the first portion and the second portion includes a locating feature configured to locate the second portion relative to the first portion.

12. The contact pin assembly of claim 1, wherein the first and second portions are secured together by one of welding, brazing, crimping, and adhesives.

13. An exhaust gas sensor comprising:
   a sensor element configured to communicate with an exhaust gas of an internal combustion engine; and
   a contact pin assembly electrically connected to the sensor element, the contact pin assembly including:
      a first portion configured to engage the sensor element; and
      a second portion configured to be connected to the first portion in either of a first configuration, wherein the contact pin assembly has a first overall length, or a second configuration, wherein the contact pin assembly has a second overall length less than the first overall length;
      wherein the second portion is selectively connected to the first portion in the first configuration or the second configuration depending on a length of the exhaust gas sensor.

14. The exhaust gas sensor of claim 13, wherein the second portion is configured to be connected to the first portion in more than two configurations.

15. The exhaust gas sensor of claim 14, wherein the first portion includes a base configured to engage the sensor element and a hollow stem extending from the base, and wherein the second portion is at least partially received inside the hollow stem.

16. The exhaust gas sensor of claim 15, wherein the second portion defines a solid rod having a first end received inside the hollow stem and a threaded second end to receive a spark-plug type post terminal.

17. The exhaust gas sensor of claim 13, wherein the first and second portions are configured to be positioned in telescoping relation with respect to one another.

18. The exhaust gas sensor of claim 13, wherein the first portion includes a base configured to engage the sensor element and a stem extending from the base, and wherein the second portion defines a tube configured to be received over at least a portion of the stem.

19. The exhaust gas sensor of claim 18, further comprising an insert having a first end received by the tube and a threaded second end to receive a spark-plug type post terminal.

20. A method of assembling an exhaust gas sensor having a sensor element and a contact pin assembly electrically connected to the sensor element, the contact pin assembly having a first portion configured to engage the sensor element and a second portion configured to be connected to the first portion in either of a first configuration, wherein the contact pin assembly has a first overall length, or a second configuration, wherein the contact pin assembly has a second overall length, the method comprising:
   determining a length of the exhaust gas sensor;
   connecting the second portion to the first portion in one of the first and second configurations depending on the length of the exhaust gas sensor; and
   after connecting the second portion to the first portion, installing the contact pin assembly in the exhaust gas sensor.

21. The method of claim 20, wherein connecting the second portion to the first portion includes placing the second portion and first portion in telescoping relation and securing the second portion and the first portion together in one of the first and second configurations.

22. The method of claim 20, wherein connecting the second portion to the first portion includes sliding the first and second portions relative to one another and securing the first and second portions together in one of the first and second configurations.

* * * * *